(12) United States Patent
Lin

(10) Patent No.: US 6,795,993 B2
(45) Date of Patent: Sep. 28, 2004

(54) ROTARY ELECTRIC TOOTHBRUSH WITH A SWING HEAD

(76) Inventor: Yuan Huang Lin, PO Box 82-144, Taipei (TW)

( * ) Notice: Subject to any disclaimer, the term of this patent is extended or adjusted under 35 U.S.C. 154(b) by 171 days.

(21) Appl. No.: 10/158,937

(22) Filed: Jun. 3, 2002

(65) Prior Publication Data

US 2003/0221268 A1 Dec. 4, 2003

(51) Int. Cl.[7] .............................................. A46B 13/00
(52) U.S. Cl. .............................. 15/28; 15/22.2; 15/22.4
(58) Field of Search ................................ 15/22.1, 22.2, 15/22.3, 22.4, 28

(56) References Cited

U.S. PATENT DOCUMENTS

| 4,326,314 A | * | 4/1982 | Moret et al. ................. 15/22.1 |
| 5,381,576 A | * | 1/1995 | Hwang ........................ 15/22.1 |
| 5,625,916 A | * | 5/1997 | McDougall .................... 15/28 |
| 5,732,432 A | * | 3/1998 | Hui ............................. 15/22.1 |
| 2003/0126699 A1 | * | 7/2003 | Blaustein et al. ............ 15/22.2 |

* cited by examiner

Primary Examiner—Laura C Cole
(74) Attorney, Agent, or Firm—Leong C. Lei

(57) ABSTRACT

An electric toothbrush comprised of a handle and a neck; the handle containing a swing link connected to a motor and a cell cabinet; the neck also containing a crank to drive a brush head and another swing link abutted to its counterpart in the handle characterized by that a rotor being inserted to the motor shaft; a U-shape member inserted to the swing link in the handle; the U-shape member being engaged by friction due to reciprocal impact from the rotor thus to drive the swing link in the neck; and the crank further driving the brush head to execute lateral swing at an angle of thirty degrees to achieve the optimal tooth brushing effect.

4 Claims, 6 Drawing Sheets

ROTARY ELECTRIC TOOTHBRUSH WITH A SWING HEAD

BACKGROUND OF THE INVENTION (a) Field of the Invention

The present invention is related to an electric toothbrush, and more particularly, to one that converts the rotation of the brush head into lateral swing to achieve optimal tooth brushing effect.

(b) Description of the Prior Art

Improper tooth brushing pattern or habit not only fails to clean the teeth but also damages the gum to such extent beyond remedy. Therefore, correct and regular tooth brushing is the best way to maintain oral cavity hygiene and health. According to orthodontic documentation, the best way to brush one's teeth is to laterally or vertically brush them depending on the contact surface of the teeth. However, the brush head of electric toothbrushes generally available in the market fail to provide rotation and swing at the same time.

SUMMARY OF THE INVENTION

The primary purpose of the present invention is to provide an electric toothbrush with a brush head that is capable of executing swing while rotating. To achieve the purpose, the present invention is comprised of a handle and a neck. The handle contains a swing link connected to a motor and a battery cabinet. The neck contains a crank to drive the brush head, and another swing link abutted to the swing link provided in the handle characterized by that a rotor is inserted to the motor shaft and a U-shape member is provided to the swing link in the handle to simplify the structure of the driving end of the motor since no gear is required. The U-shape member is engaged by friction due to reciprocal impact from the rotor thus to drive the swing link in the neck; and the crank further driving the brush head to execute lateral swing at an angle of thirty degrees to achieve the optimal tooth brushing effect.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown byway of illustrative example.

DETAILED DESCRIPTION OF THE PREFERRED EMBODIMENT

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
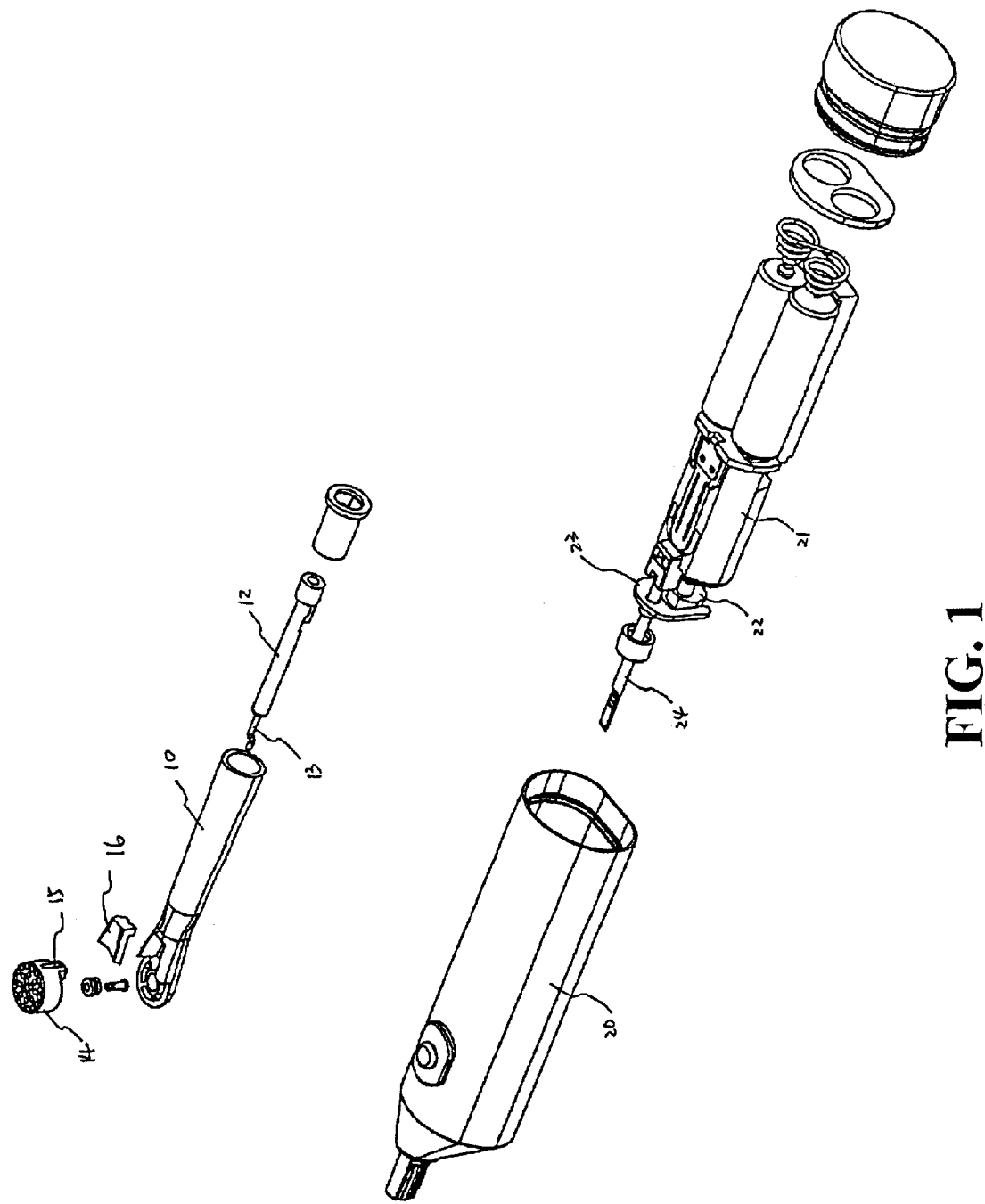
FIG. 1 is a perspective view of the present invention.
Figure 2:
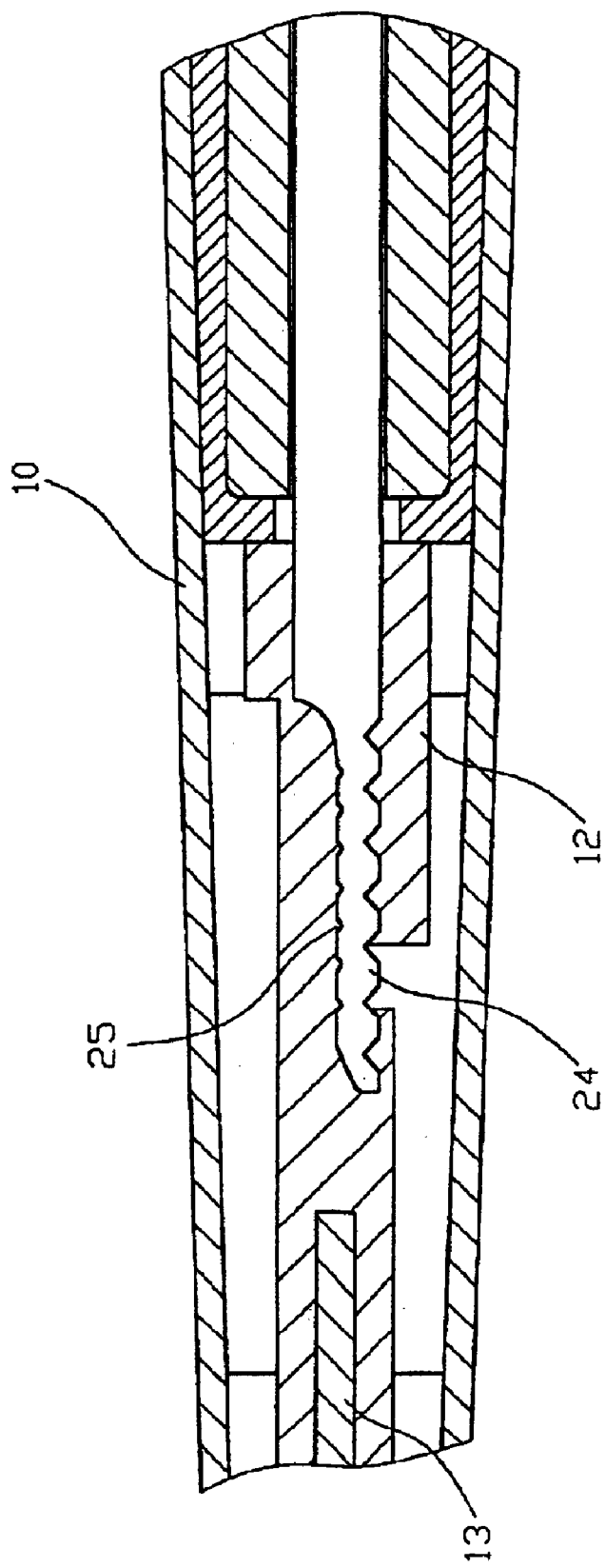
FIG. 2 is a sectional view showing the connection of a main unit and a replaceable neck of the present invention.
Figure 6:
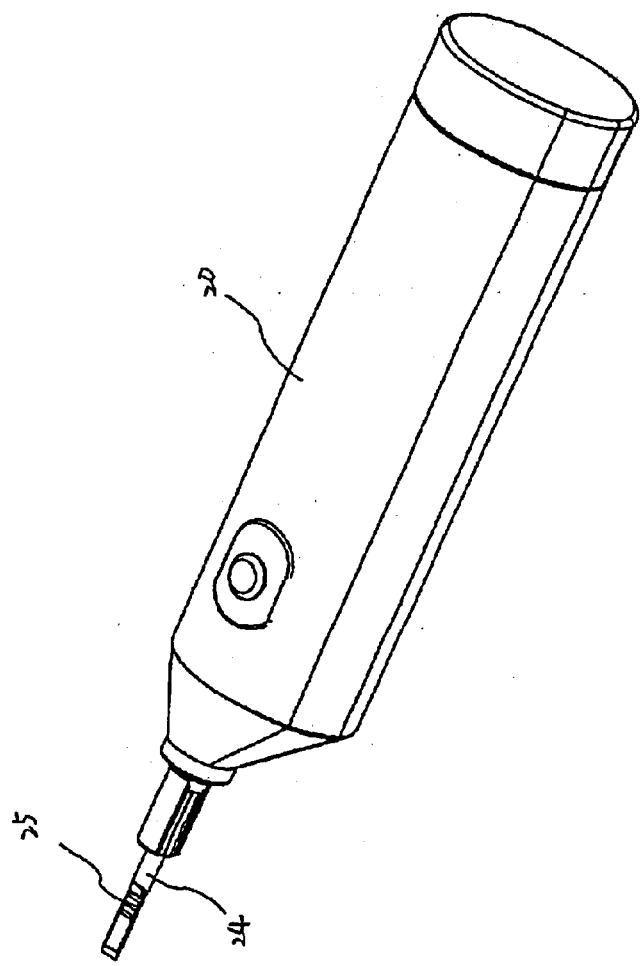
FIG. 6 is a perspective view showing that both of the neck and the main unit of the present invention being ready for connection.
Figure 6:
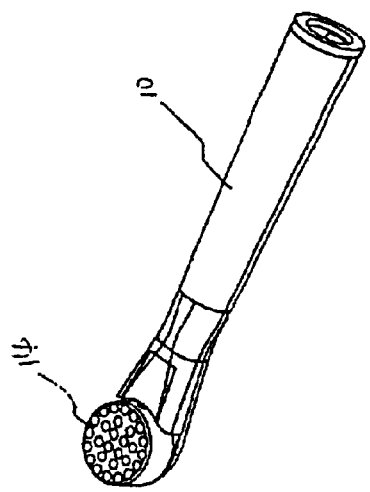

Referring to FIGS. 1 and 2, an electric toothbrush of the present invention is essentially comprised of a handle 10 and a neck 20. FIG. 6 shows that both of the handle 10 and the neck 20 are respectively assembled ready for engaging to each other. The handle 10 contains a swing link 24 made of metallic material connected to a drive motor 21; a battery cabinet, an rotor 22 in a form of a wedge, a U shape member inserted to the swing link 24 that drives the main unit to swing, and the rotor 22 merely being placed inside the U shape member 23.

The neck 20 is comprised of a crank 13 to drive a brush head 14, and a swing link 12 engaged to the metal swing link 24 on the shaft of the motor 21 in the handle 10 of the main unit. The tip of the metal swing link 24 indicates semi-circular plane with a triangle gap 25 to be held in position with the swing link 12 inside the neck 20. The location where the swing link 12 is held in position inside the neck 20 compromises the shape of the tip of the metal swing link 24. Both links 12, 24 are abutted to each other as illustrated in FIG. 2. Wherein, a stainless steel crank 13 is provided to the tip of the swing link 12 in the neck 20. The tip of the crank 13 is inserted into a groove 15 provided by the circumference of the bottom of the brush head 14.

The present invention is characterized that the rotary shaft of the drive motor 21 is inserted with a rotor 22 and the U-shape member 23 is inserted to the swing link 24 in the main unit. Accordingly, the U-shape member 23 is reciprocally hit by the rotor 22 to drive the swing link 24 in the neck 10, thus to cause the crank 13 to drive the brush to reciprocally swing for thirty degrees sideways to achieve optimal tooth brushing effect.

Figure 3A:
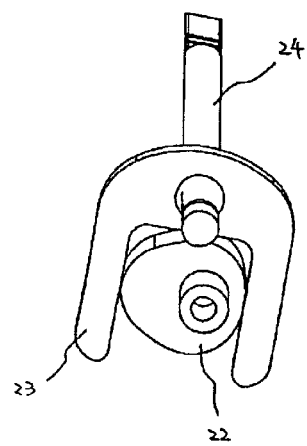
FIGS. 3A, 3B and 3C are schematic views showing the swing direction of a swing link provided in the main unit of the present invention.
Figure 3B:
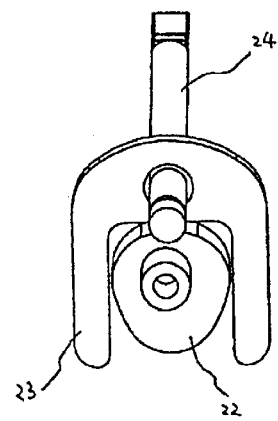
Figure 3C:
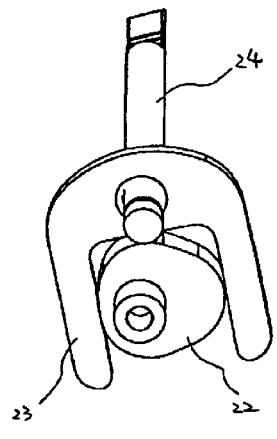

Now referring to FIGS. 3A, 3B and 3C, the rotor 22 is inserted to the shaft of the motor 21, and the U-shape member 23 is merely inserted to the rotor 22. The swing link 24 in the main unit is inserted to a hole in the U-shape member 23 while one end of the swing link 24 is fixed to the casing of the main unit. Once the motor 21 drives the rotor 22, the rotor 22 continuously executes circumferential rotation. When the tip of the rotor 22 tame to hold against one side of the U-shape member 23, the U-shape member 23 swings and leans to that side. Once the rotor 22 returns to its central position, the U e-shape member 23 also returns to its central position. Later as the rotor 22 turns and shifts to another side of the U-shape member 23, the U-shape member 23 swings and leans to that side as driven by the motor 21 for the rotor 22 to complete a cycle of circumferential rotation as driven by the motor 21. Meanwhile, the U-shape member 23 as linked to the rotor 22 executes reciprocal swing for the swing link 24 to swing up and down while moving in a horizontal direction.

Figure 4C:
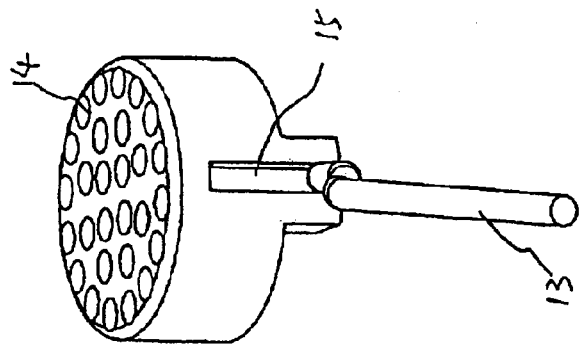
FIGS. 4A, 4B and 4C are schematic views showing that the lateral swings by another swing link in the neck being converted to lateral rotation by a brush head.
Figure 4B:
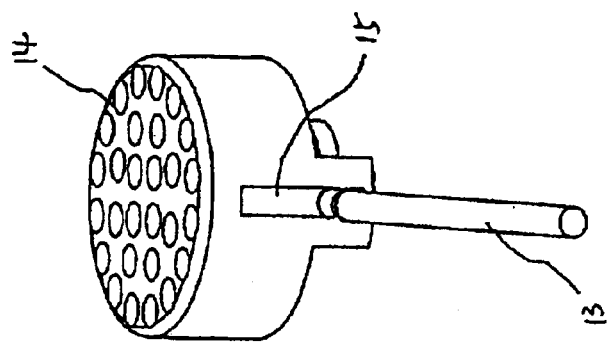
Figure 4A:
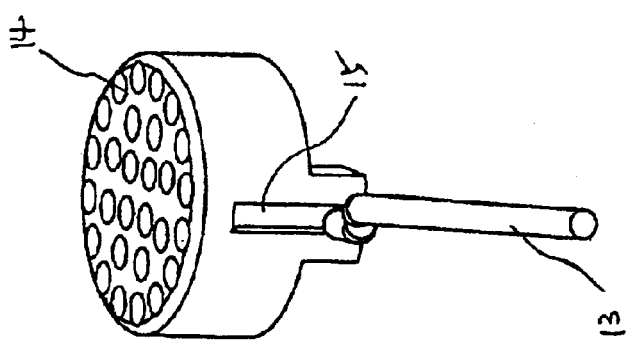

As illustrated in FIGS. 4A, 4B and 4C, the lateral swing executed by the swing link 12 in the neck 20 is converted into the lateral rotation by the brush head 14 that is provided vertical to the swing link 12. Wherein, the swing link 12 in the neck 20 is securely abutted to the semi-circular plan and the triangle gap 25 of the swing link 24 inside the main unit. A crank 13 is connected to the swing link 12 in the neck 20 and is received in the groove 15 provided on one side to the circumference of the brush head 14. Accordingly, once the crank 13 is laterally driven by the swing link 12, the brush head 14 is further driven to swing backwardly at an angle of thirty degrees.

Figures 5, 5A:
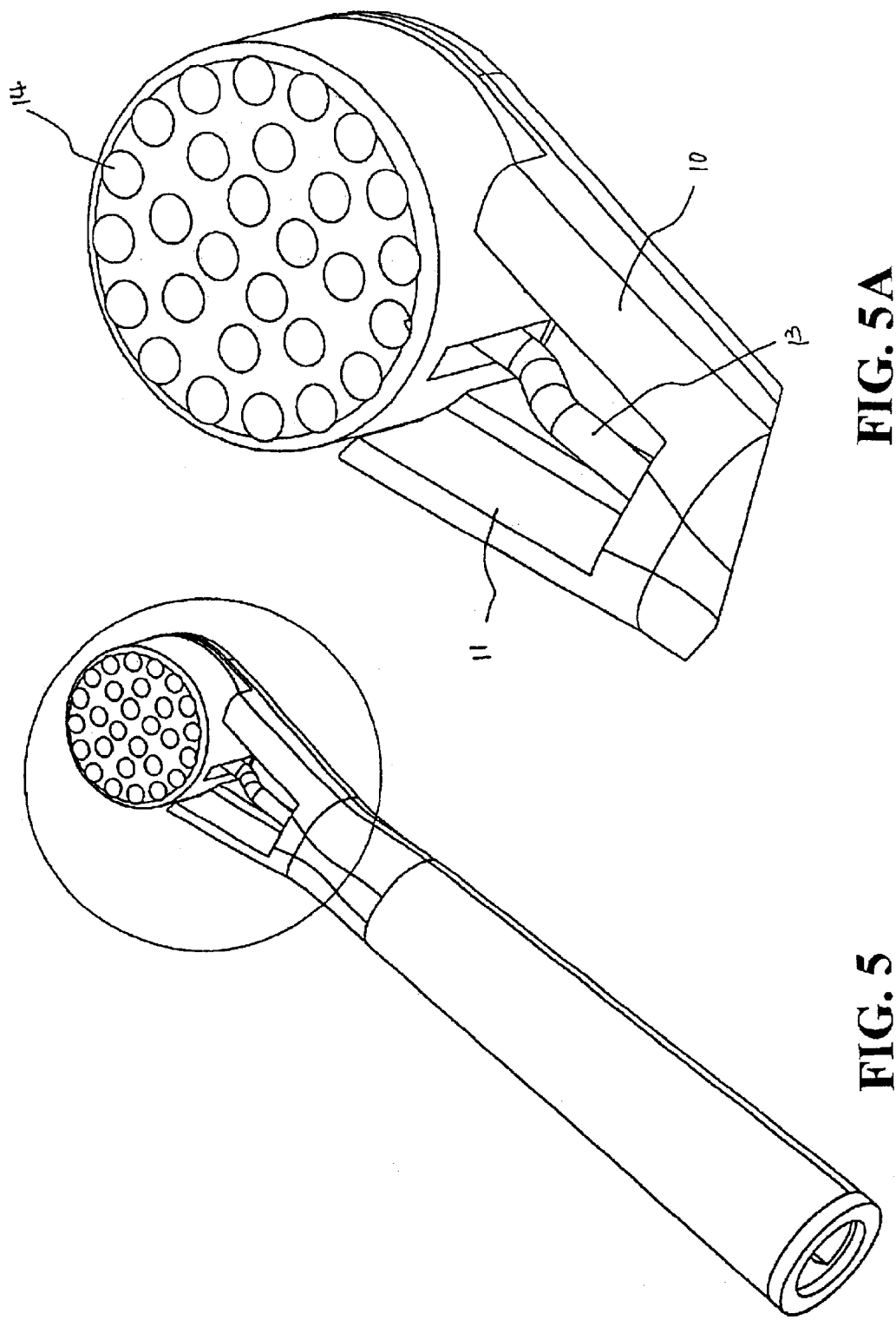
FIG. 5 is a schematic view showing that a cover to prevent the brush head of the present invention from falling off.
FIG. 5A is an enlarged view of a portion of FIG. 5.

As illustrated in FIGS. 5 and 5A, the brush head 14 is prevented from falling off in the present invention by means of a casing 16. Wherein, a recess 11 is reserved on the front edge of the neck 20 when the front of the neck 20 is inserted with the crank 13 and the brush head 14. The recess 11 allows inspection of the groove 15 where the crank 13 is connected to the brush head 14. The groove 15 then is closed with the casing 16 to prevent the brush head 14 from falling during the use of the toothbrush.

FIG. 6 is a perspective view showing that both of the neck and the main unit of the present invention being ready for connection.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A rotary electric toothbrush with a swing head comprising a handle and a neck, the handle containing a first swing link connected to a motor, the neck containing a crank to drive a brush head, and second swing link to be abutted to the first link in the handle, wherein a rotor is attached to a motor shaft; a U-shape member being attached to the first swing link at an upper edge of the handle; the first swing link indicating a semi-circular plan with a triangle gap to drive the second swing link in the neck when the U-shape member having motion caused by friction from the rotor; the brush head being driven by the crank to execute lateral swing of thirty degrees respect to a vertical axis; and wear and tear to the crank being minimized so there is little resistance being transferred to the rotating crank; a bottom of a front end of the neck and a plastic part of the crank that is held in position by the brush head and are secured.

2. A rotary electric toothbrush with a swing head as claimed in claim 1, wherein a groove is provided around a front end of the crank at where the crank is held in position by the brush.

3. A rotary electric toothbrush with a swing head as claimed in claim 1, wherein a rotor in form of a wedge is inserted to the motor shaft to to frictionally impact the U-shape member in the handle when the rotor rotates for the U-shape member to swing.

4. A rotary electric toothbrush with a swing head as claimed in claim 1, wherein a swing motion by the swing link in the neck is converted into lateral rotation of the brush head as driven by the swing motion of the swing link in the handle.

\* \* \* \* \*